United States Patent [19]

Gardano et al.

[11] Patent Number: 4,536,595
[45] Date of Patent: Aug. 20, 1985

[54] PROCESS FOR THE PREPARATION OF ALPHA-ARYL-PROPIONIC ACIDS AND ALKALINE SALTS THEREOF

[75] Inventors: Andrea Gardano, Trino Vercellese; Franco Francalcanci; Marco Foà, both of Novara, all of Italy

[73] Assignee: Montedison S.p.A., Milan, Italy

[21] Appl. No.: 419,616

[22] Filed: Sep. 17, 1982

[30] Foreign Application Priority Data

Sep. 21, 1981 [IT] Italy ............................... 24054 A/81

[51] Int. Cl.³ ............................................. C07C 51/10
[52] U.S. Cl. ...................................... 562/406; 549/66; 549/79
[58] Field of Search ...................... 562/406; 502/159; 549/66, 79

[56] References Cited

U.S. PATENT DOCUMENTS

| | | | |
|---|---|---|---|
| 3,116,306 | 12/1963 | Heck | 562/406 |
| 3,708,529 | 1/1973 | Cassar | 562/406 |
| 3,928,429 | 12/1975 | El-Chahawi | 562/406 |
| 4,111,856 | 9/1978 | Haag | 502/159 |
| 4,152,352 | 5/1979 | Perron | 562/406 |
| 4,351,952 | 9/1982 | Foa | 562/406 |

*Primary Examiner*—Michael L. Shippen

[57] ABSTRACT

Alpha-arylpropionic acids and alkaline salts thereof are prepared by catalytic reaction with carbon monoxide of the corresponding secondary halids in an anhydrous low alcohol solvent in the presence of a salt of cobalt hydrocarbonyl and in further presence of alkaline hydroxides under substantially ambient temperature and pressure conditions.

The products obtained find useful applications in the field of pharmaceutics (analgesics, antipyretics, etc.) and as intermediates for chemical syntheses of fine chemicals, phytodrugs, etc.

16 Claims, No Drawings

PROCESS FOR THE PREPARATION OF ALPHA-ARYL-PROPIONIC ACIDS AND ALKALINE SALTS THEREOF

BACKGROUND OF THE INVENTION

The following formula (I) can be attributed to the alpha-arylpropionic acids obtainable according to the present invention:

wherein Ar represents either an aromatic, or a heteroaromatic group containing one or more rings, however linked together, having globally up to 20 carbon atoms, such as phenyl-, naphthyl-, diphenyl- and thienyl groups. Said Ar group may in its turn also be substituted by groups inert under reaction conditions. Compatible groups are e.g.: alkyl-, cycloalkyl- and aryl-groups, also optionally substituted, halogens, alkoxyl groups, phenoxyl groups, ketonic groups.

Only recently research has turned towards carbonylation of substrates of the secondary benzyl type, such as for instance secondary aryl-alkyl halids, which carbonylation, besides considerations on the reaction mechanism involved, meets also operational difficulties with regard to the possible yields, etc.

Prior Art literature on the matter is not particularly exhaustive, especially with regard to the aspect of the commercial production.

It can, however, practically be stated that, up to this date, the alpha-aryl-propionic acids and the alkaline salts thereof, object of the present invention, were prepared by hydrolysis of the corresponding nitriles; or by reaction of $CO_2$ with Grignard compounds; or by, the decarbonylation of malonic derivatives or else by oxidation of structurally suitable alcohols or aldehydes, or finally by reduction of aryl-acrylic acids etc.

It is a question of methods technologically removed from the process object of the present invention, which methods are characterized by the fact of being polystages, non-catalytic and essentially complicated by the use of reactants difficult to be found and/or handled, with the resulting corresponding operational and economical burdens which make such methods of little practical commercial attractiveness.

On the other hand, there have recently been suggested catalytic methods for the preparation of alpha-aryl-propionic acids.

According to one of these methods, substituted alpha-aryl-propionic acids or alkyl esters thereof are prepared by means of either hydrocarboxylation or hydrocarbalkoxylation of substituted aryl-ethylenes in an aqueous or alcoholic medium, catalyzed by Palladium complexes, preferably in the presence of acids.

Nevertheless, the commercial interest offered by the above mentioned method does not seem high. As a matter of fact, the method foresees, amongst others, the use of expensive Pd complexes as catalysts and of very high CO pressures.

There have also been reported possibilities for carbonylation reactions of halogen derivatives of the secondary benzyl type with Pd and Co complexes.

In the first instance, there has been foreseen the use of expensive catalysts such as arsinic Pd complexes, under CO pressure. Moreover, the esters are obtained with rather poor yields and selectivities.

In the second instance, the method foresees the formation of esters using alkaline alcoholates in the presence of dicobalt-octacarbonyl. In this latter case, too, the yields and selectivities that are obtainable by the method are rather poor. In fact, there are substantially obtained quantities of ethers and esters of the linear acid. This involves however operational burdens in the separation and purification of the products.

Moreover, a further economical burden is represented by the use of alcoholates under strictly controlled pH conditions.

Finally, the reaction proves to be limited to the phenyl derivatives only, possibly only alkyl-substituted derivatives.

OBJECT OF THE INVENTION

The present invention concerns a process for the preparation of alpha-aryl-propionic acids of formula (I), above defined and of alkaline salts thereof.

More particularly the present invention concerns a process for the preparation of alpha-arylpropionic acids and of their alkaline salts, by means of a synthesis starting from the corresponding organic halids and carbon monoxide in the presence of a catalytic system based on cobalt carbonyl complexes and of alkaline metal hydroxides.

From the alkaline salt the acid is easily obtained by acidification, extraction, etc. according to conventional methods.

The process is based on the carbonylation reaction of 1-halogen-1-arylethanes with the insertion of the carboxylic group onto a secondary carbon atom, under catalysis conditions afforded by carbonylic complexes of Co, and in the presence of alkaline hydroxides.

The compounds thus obtained are interesting products for their useful use within a wide range of commercial applications.

In fact they constitute important products for carrying out organic syntheses in general, with specific possibilities in the field of so-called fine chemicals, phytodrugs, and especially in the field of pharmaceutical products.

More particularly, products falling under this class, such as for instance 2-(4'-isobutylphenyl)-propionic acid and 2-(6'-methoxy-2'-naphthyl)-propionic acid, are of a particular interest in the field of pharmaceutical products, as antiphlogistic agents, analgesics, antipyrethics, etc.

THE PRESENT INVENTION

Thus, it is an object of this invention to provide a simple and economical catalytic process suited for the commercial preparation of the acids of formula (I) or of their alkaline salts, which process is free of the drawbacks cited in the discussed Prior Art.

In fact, according to the present invention, a process is provided for the carbonylation of secondary benzyl-halogenid substrates on the secondary carbon atom, under simple operational conditions, by using as a catalyst an inexpensive Co hydrocarbonyl salt that may be supported and thus easily removable in order to be reused in a successive cycle, as well as cheap and practical basic agents in an anhydrous alcoholic medium. A process will thereby be achieved which will ensure an applicational flexibility that will allow to obtain selectively and with satisfactory yields a much wider range of alpha-arylpropionic acid products and/or of their alkaline salts, practically operating at a lower temperature and under the atmospheric CO-pressure.

GENERAL DESCRIPTION OF THE INVENTION

According to this invention, there is provided a process for the preparation of alpha-arylpropionic acids of formula (I), as above defined, by catalytic reaction with carbon monoxide of the corresponding secondary halids of formula (II):

wherein: Ar has the same meaning as for formula (I),- while X is a halogen chosen from between Cl and Br, and which process is characterized in that the reaction is conducted in an anhydrous alcohol solvent medium consisting of alkanols having up to 4 carbon atoms, in the presence of alkaline hydroxides, and in the further presence of a catalytic system consisting of a cobalt hydrocarbonyl salt, optionally supported on resins, or of its precursors, at a temperature comprised between 0° C. and 50° C. and at about substantially atmospheric pressure.

The reaction may be schematically represented by the following equation:

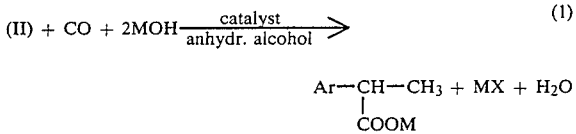

wherein the given symbols have the known meaning and where M stands for K, Na, Li. The free carboxylic acid (I) is then easily obtained from the alkaline salts by displacement with strong acids (HCl, H$_2$SO$_4$), extraction with solvents, etc., according to conventional methods.

The catalytic system consisting of a cobalt hydrocarbonyl salt may work either dissolved in the anhydrous alcoholic medium, and in this case the reaction is conducted in a homogeneous phase, or supported on anion exchanging resins which will be more precisely defined further on.

The reaction medium will thus turn out to be heterogeneous while the reaction proceeds according to the corresponding procedures and techniques.

The alcoholic solvent medium is chosen from amongst: anhydrous methyl alcohol, ethyl alcohol, isopropyl alcohol, propyl and butyl alcohols.

The alkaline base is chosen from amongst: sodium, potassium and lithium hydroxides, which are admixed to the reaction mixture as solids. There may be used for this purpose the corresponding commercial products.

The catalysts are cobalt hydrocarbonyl salts of the following formula

wherein Me stands for a cation of a metal having valency n, such as for instance alkaline metals (Na, K, Li) or cobalt, iron, manganese, etc., that are quite known and easily preparable according to conventional methods.

Preferred catalysts are: sodium, cobalt, manganese and iron salts of formula (III).

Likewise, there may also be used compounds that are precursors of the above mentioned cobalt hydrocarbonyl salts.

By the term "precursor" in this description there are indicated one or more compounds which, under reaction conditions, will give place to the above indicated cobalt hydrocarbonyl salt.

For instance, the cobalt hydrocarbonyl catalyst salt may be obtained from a cobalt salt such as for instance chloride, sulphate, bromide, etc., a Fe-Mn powder alloy (containing about 80% of Mn) and from sulphurated promoters, in the desired alcohol (methyl, ethyl alcohol, etc.) under a carbon monoxide pressure comprised between 1 and 20 atmospheres and at temperatures comprised between 10° C. and 80° C., preferably comprised between about 25° and 35° C.

The concentration of cobalt salt in the solution is comprised between 0.3 and 1mol/liter. For each mol of cobalt salt there are used from 1 to 2 mols of Mn in the form of a Fe/Mn alloy. This Fe/Mn alloy is ground beforehand so that it will pass through a screen of at least 5000 meshes/sq.cm.

Preferred sulphurated promoters are sodium sulphite and sodium thiosulphite, which are used in quantities comprised between 0.01 and 0.1 mol/mol of cobalt salt.

The alcoholic mixture containing the cobalt salt, the alloy and the sulphurated promoter in the alcoholic solvent, is kept in a CO atmosphere under vigorous stirring, for a time sufficient for achieving the complete absorption of the CO; a stretch of time equal to at least 2 up to 3 hours. In this way there are obtained the Mn and/or Fe salts of the cobalt hydrocarbonyl in alcohol solution.

Alternatively, the catalyst alkaline salt of the Co hydrocarbonyl may be obtained "in situ" from Co$_2$(CO)$_8$ which, in the basic conditions present in the reaction medium, gives place to the Co hydrocarbonyl salt; or, separately, the sodium salt may be obtained from Co$_2$(CO)$_8$ through the reduction with a sodium amalgam in an ether solvent (tetrahydrofurane); while the Co$_2$(CO)$_8$ is prepared for instance from CoCO$_3$ under a CO and hydrogen pressure in petroleum ether.

Effective resins, suitable as carriers for the cobalt hydrocarbonyl salt catalyst, are preferably the resins having a styrenic, acrylic or polycondensated matrix. They are characterized by the presence of at least one strongly basic functional group of formula (IV) and (V):

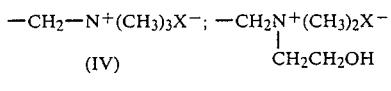

or by a medium basic functional group (VI):

wherein X has the meaning already previously given.

The resins may, moreover, be either of the gel type or of porous, of isoporous or macroporous type. As particularly effective resins turned out to be the following resins: AMBERLYST A26 (IV); A27 (IV); A29 (V); AMBERLITE IRA 402 (IV) and IRA 93 (VI)(all trade marks of Röhm & Haas); KASTEL A 101 (VI) and A 500P (IV) (trade marks of MONTEDISON S.p.A.).

Supporting of the catalyst onto the carrier is easily achieved by bringing the resin into contact with an alcohol solution of the previously prepared catalyst, optionally after the resin had preliminarily been washed with alcohol, preferably with the same alcohol of the reaction, for eliminating any moisture therein contained.

This contact occurs e.g. by immersion of the resin into the catalyst solution.

The resin is used in an at least stoichiometric quantity (calculated on the equivalent groups/g) with respect to the quantity of catalyst, so that after a short conntact time, the catalyst itself will turn out to be completely supported by the resin.

The control is provided by the absence of $Co(CO)_4^-$ ions in the I.R. analysis of the solution and by the presence of the same ions in the polymeric matrix. In general, for this purpose, there will suffice short times of the order of magnitude between about 1 and 60 minutes.

Effective alcohols have proved to be methyl, ethyl and isopropyl alcohol.

Effective alkaline hydroxides have proved to be NaOH and KOH hydroxides.

In order to ensure a selective carbonylation reaction on the secondary carbon atom, the above specified hydroxides are admixed to the reaction mixture in the solid state in the alcohol medium, in quantities equal to at least 2 mols per each mol of substrate (II).

The concentration of the alkaline hydroxide is comprised between about 10 and 100 grams per liter of solvent.

Moreover, the addition of the alkaline hydroxides may be carried out in one single operation at the beginning of the loading of the reactants; in fact it is not necessary a special control of the pH value. The halide (II) is admixed, as the case may be, either in one single operation or gradually in single batches, or else in a continuous way through time.

The concentration of the halide in the alcohol medium is maintained at values comprised between about 40 and 200 g/l of solvent.

The cobalt hydrocarbonyl catalyst salt, whether it is used in solution according to the homogeneous reaction, or supported on a resin, as described above according to a heterogeneous reaction, will be added in a quantity comprised between 1:5 and about 1:500, but preferably comprised between about 1:10 and 1:200, with respect to the halide of formula (II), and calculated as mols of cobalt per mols of halid (II).

The reaction temperature is comprised between about 0° C. and 50° C., but is preferably comprised between about 10° C. and 35° C.

Moreover, the reaction proves to be completed in a stretch of time comprised between 2 and 24 hours, depending on the parametrical conditions used and on the substrate (II) employed.

The pressure of the carbon monoxide is substantially the atmospheric pressure.

The carbonylation reaction is achieved by putting into contact the catalyst, optionally supported on a resin, with an anhydrous alcohol solution containing the Na or K hydroxide and the halide (II) in a carbon monoxide atmosphere. The separation of the reaction product is carried out according to conventional methods.

In the case one operates in a homogeneous phase, that is with the cobalt hydrocarbonyl catalyst salt not supported on the resin but dissolved in the alcohol medium, at the end of the reaction there is added acidulated water, acidulated with mineral acids (HCl, $H_2SO_4$) and the solution is then extracted with ethyl ether.

The ether extract is then washed with an aqueous solution saturated with $NaHCO_3$ or with a 10% soda, and the aqueous extract is then acidified with mineral acids and extracted again with ethyl ether.

After evaporation of the ether, there is obtained the desired alpha-aryl-propionic acid.

In case, however, that one operates according to the method of the reaction conducted in a heterogeneous phase, the cobalt hydrocarbonyl catalyst salt, carried by the resin, is separated by filtering and the resin is then washed with a hydroalcoholic mixture.

The resin thus separated may be used for a subsequent carbonylation reaction, optionally after restoring the used up catalyst. The regeneration of the resin is carried out after a certain number of cycles, when all the supported catalyst is practically exhausted, by simply washing the resin with an aqueous solution of hydrochloric acid.

In this way all the cobalt passes practically into the aqueous solution and the resin, separated by filtering said aqueous acid solution, washed with water and alcohol, is ready for a subsequent supporting of the catalyst.

The filtrate, combined with the washings carried with the hydroalcoholic mixture, is then treated as previously described in connection with the reaction in a homogeneous phase.

Halides (II), containing a secondary carbon atom and suited for use in the carbonylization reaction according to this invention have proved to be: 1-bromo-1-phenylethane; 1-chloro-1-phenylethane; 1-bromo-1-(p-chlorophenyl)-ethane; 1-chloro-1-(6'-methoxy-2'-naphthyl)-ethane, 1-chloro-1-(p-isobutylphenyl)ethane.

According to a practical processing method, the invention may be carried out in the following way.

Into a reactor, fitted with a stirrer, a temperature regulating and reactant feeding system, there is added to the alcohol solvent, under a carbon monoxide head, the freshly prepared catalyst, optionally supported on a resin, and the alkaline hydroxide, in the wanted ratio.

The solution or suspension thus obtained is then submitted to stirring. Then, and still under a carbon monoxide head, the reaction mass is additioned with halide (II) in the desired ratio.

The reaction mixture is then kept under stirring at the desired temperature, under a CO head, for the time necessary for observing the end of the absorption of the CO. Once this absorption has stopped, the reaction mixture is treated as previously described for the separation of the products.

The process, object of this invention, proves particularly convenient, as previously illustrated, in particular, as a whole, for the mild operational conditions, for the use of inexpensive reactants, for its selectivity and flexibility in the application to the secondary halides of the benzyl type, even substituted, according to a wide range of possible products.

Finally, the catalyst is simple to prepare and, in case one operates with a supported catalyst, the process proves particularly interesting, from the operational point of view, thanks to the possibility of operating in a continuous way with an easy recovery, regeneration and re-cycling of the catalytic system.

SPECIFIC DESCRIPTION OF THE INVENTION

The invention will now be further described by the following examples, given for merely illustrative purposes.

Example 10 is given in order to evidence the criticality of the operational parameters of this process. In said example, it will in fact be noticed that, when operating in the presence of a hydro-alcoholic mixture, instead of an anhydrous alcohol, besides the desired product, there will also be obtained substantial quantities of the isomer linear acid (beta-phenylpropionic acid).

EXAMPLE 1

Into a 100 ml flask, provided with a magnetic stirrer, a thermometer and a coolant, under a CO head there were introduced 2 g of NaOH, 22 ml of ethanol, 3 ml of a catalyst solution (2 g of Co as $Co(CO_4)^-$ cobaltate in 100 ml), prepared from 20 g of $CoCl_2.6H_2O$, 0.6 g of $Na_2S.9H_2O$, 1.5 g of $Na_2S_2O_3.5H_2O$, 10 g of a powdery Mn/Fe alloy passing through a 5000 mesh/sq.cm screen, 180 ml of ethanol, and carbon monoxide under atmospheric pressure, until the end of the CO absorption.

The temperature was brought to 10° C. and 4 g of 1-bromo-1-phenylethane were all at once introduced.

The reaction mixture was then left under stirring for 16 hours, maintaining during said period the temperature between 10° and 15° C.

Thereupon there was admixed water, acidulated with HCl, and the mixture was then extracted with ethyl ether. The thus obtained extract was thereupon washed with an aqueous solution of $NaHCO_3$. The resulting alkaline solution was then again acidified and extracted with ethyl ether. By evaporating the extracting ether there were obtained 2.5 g of alpha-phenylpropionic acid or hydratropic acid with a yield equal to 77% calculated on the halide used.

EXAMPLE 2

In the same equipment described in example 1, under a CO head, there were introduced: 2 g of NaOH, 22 ml of ethanol, 3 ml of the catalyst solution prepared as described in example 1.

The temperature was then brought up to 30° C. and 3.2 g of 1-chloro-1-phenyl-ethane were introduced. The reaction mixture was left under stirring for 16 hours by keeping the temperature at 30° C. The reaction mixture was allowed to cool down to room temperature and it was then proceeded as described in example 1, thereby obtaining 1.85 g of hydratropic acid (54% yield).

EXAMPLE 3

Into the same equipment described in example 1, under a CO head, there were introduced:
2 g of NaOH, 22 ml of ethanol, 3 ml of catalyst solution prepared as described in example 1.

The temperature was thereupon brought to 10° C. and into the reactor were introduced 4.8 g of 1-bromo-1-(p.chloro-phenyl-) - ethane. The reaction mixture was kept under stirring for 16 hours at a temperature comprised between 10° C. and 15° C.

Thereupon it was proceeded as in example 1, obtaining 2.8 g of 2-(p.chlorophenyl)-propionic acid having the following formula:

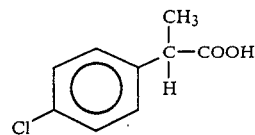

with an actual yield of 69.4%.

EXAMPLE 4

Into the same equipment described in example 1, under a CO head, there were introduced:
1.2 g of NaOH; 50 ml of isopropyl alcohol; 0.25 g of $Co(CO)_8$.

The temperature was then brought to 15° C. and the reaction mixture was additioned with 2.5 g of 1-chloro-1-( 6'-methoxy-2'-naphthyl)-ethane of the formula:

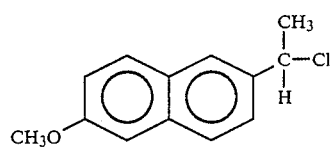

This reaction mixture was maintained under stirring for 8 hours by keeping temperature at 15° C. Thereupon it was proceeded according to that described in example 1, thereby obtaining 1.5 g of 2-(6'-methoxy-2'-naphthyl)-propionic acid of the formula:

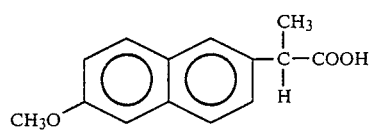

with a yield of 57.7%.

EXAMPLE 5

Into the same apparatus as that described in example 1, under a CO head, there were introduced: 2 g of NaOH; 22 ml of ethanol; 3 ml of a catalyst solution prepared as described in example 1. Temperature was brought to 20° C. and 3.45 g additioned of 1-chloro-1-(p.isobutylphenyl)-ethane of the formula:

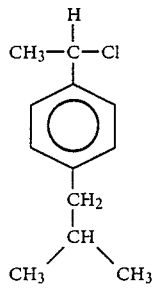

The reaction mixture was thereupon submitted for 16 hours to stirring by keeping temperature at 20° C. It was then proceeded as described in example 1, using however a 10% aqueous solution of NaOH for extracting the acid fraction. Thereby were obtained 2.6 g of 2-(p.isobutylphenyl)-propionic acid of formula:

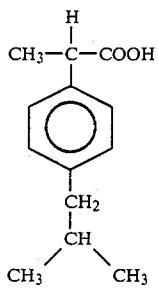

with a yield of 71.9%.

EXAMPLE 6

Into the same apparatus described in example 1, under a CO head, there were introduced: 45.5 ml of ethanol; 4.5 ml of a catalyst solution prepared according to the procedures used in example 1, and 4 g of AMBERLYST A26 resin, previously washed with ethanol, and dried.

The suspension was thereupon submitted to stirring for 15 minutes at room temperature so as to support completely the catalyst on the resin (disappearance in the ethanol solution of the I.R. band, characteristic for cobaltate).

Thereupon were added 2 g of NaOH and, after bringing the temperature to 15° C., there were added 4 g of 1-bromo-1-phenylethane. The mixture was then maintained under stirring for 16 hours, maintaining the temperature at between 10° C. and 15° C.

The resin was then filtered by washing it with a hydroalcoholic ethanol/$H_2O$ mixture.

The filtered solution was thereupon treated as described in example 1, whereby there were obtained 1.5 g of hydratropic acid, with a yield of 46.2%.

The filtered resin was ready for use in a subsequent cycle.

EXAMPLE 7

Into the same apparatus used in example 1, under a CO head, there were introduced: 2 g of NaOH; 25 ml of ethanol; 0.2 g of NaCo(CO)$_4$. The mixture was thereupon brought to a temperature of 10° C. and additioned with 4 g of 1-bromo-1-phenylethane. The reaction mass was then subjected to stirring for 16 hours at a temperature comprised between 10° C. and 15° C.

It was then proceeded as in example 1, thereby obtaining 2.45 g of hydratropic acid, with an actual yield of 75.5%.

EXAMPLE 8

Into the same apparatus used in example 1, under a CO head, there were introduced 2 g of NaOH; 50 ml of methanol; 0.2 g of NaCo(CO)$_4$.

The temperature was thereupon brought to 20° C. and into the reactor were introduced 4 grams of 1-bromo-1-phenylethane. The reaction mass was then submitted to stirring for 5 hours at a temperature maintained at 20° C.

It was then proceeded as in example 1, and there were obtained 1.72% g of hydratropic acid with a yield of 53%.

EXAMPLE 9

Into the same apparatus as that used in example 1, under a CO head, there were introduced: 2 g of NaOH, 22 ml of ethanol, 3 ml of a catalyst solution prepared as described in example 1.

The whole was then brought up to a temperature of 23° C. and into it were introduced 4 g of 1-bromo-1-phenylethane. The reaction mass was then submitted to stirring for 5 hours at a temperature maintained at 23° C.

Thereupon it was proceeded as in example 1, thereby obtaining 2.1 g of hydratropic acid, with a yield of 64.7%.

EXAMPLE 10

Into the same apparatus as that described in example 1, under a CO head, there were introduced: 2 g of NaOH; 22 ml of ethanol; 3 ml of a catalyst prepared as in example 1, and 5 ml of water.

The temperature was thereupon brought to 23° C. and the reaction mixture was additioned with 4 g of 1-bromo-1-phenylethane. The reaction mixture was then subjected to stirring for 5 hours by keeping temperature at 23° C.

Thereupon it was proceeded as in example 1. There thus obtained 2 g of hydratropic acid with a yield of 61.7% and 0.2 g of hydrocinnamic acid with a yield of 6.2%.

EXAMPLE 11

Into the same apparatus described in example 1, under a CO head, there were introduced: 2.5 g of KOH; 22 ml of ethanol; 3 ml of a catalyst prepared as in example 1. The reaction mixture was thereupon brought to a temperature of 10° C. and was then additioned with 4 g of 1-bromo-1-phenylethane. The mixture was then submitted to stirring for 16 hours at a temperature comprised between 10° C. and 15° C. It was then proceeded as in example 1, thereby obtaining 1.8 g of hydratropic acid with a yield of 56%.

What is claimed is:

1. A process for the preparation of alkaline salts of alpha-arylpropionic acids having formula (I):

wherein Ar represents an aromatic or heteroaromatic group containing one or more rings, however linked to each other, having in total up to 20 carbon atoms, by reaction with carbon monoxide, of the corresponding secondary haildes of formula (II):

wherein Ar has the same meaning as in formula (I) and where X is a halogen selected from Cl and Br, characterized in that the reaction is conducted in an anhydrous alcoholic solvent medium consisting of alkanols having up to 4 carbon atoms, in the presence of alkaline hydroxides, and in presence, as catalyst, of a salt of cobalt hydrocarbonyl, at a temperature comprised between 0° C. and 50° C. and at substantially atmospheric pressure.

2. A process according to claim 1, characterized in that the anhydrous alcoholic solvent medium is selected from the group consisting of: methyl alcohol, ethyl alcohol and isopropyl alcohol, propyl alcohol and butyl alcohol.

3. A process according to claim 1, characterized in that the alkaline hydroxide is selected from the group selected from solid sodium, potassium and lithium hydroxides.

4. A process according to claim 1, characterized in that the cobalt hydrocarbonyl salt catalyst has the formula (III):

$$Me^{n+}[Co(CO)_4]_n \qquad (III)$$

wherein Me represents a metal with valency n.

5. A process according to claim 1, characterized in that said process is conducted at a temperature comprised between 10° C. and about 35° C.

6. A process according to claim 1, characterized in that the concentration of secondary halide (II) in the alcoholic solvent medium is comprised between about 40 and 200 g/l of solvent.

7. A process according to claim 1, characterized in that the alkaline hydroxides are used according to a molar ratio of at least 2:1 with respect to the halide (II).

8. A process according to claim 1, characterized in that the concentration of alkaline hydroxide in the anhydrous alcoholic solvent medium is comprised between about 10 and 100 g/l of solvent.

9. A process according to claim 1, characterized in that the alkaline hydroxide is introduced into the alcoholic reaction solvent medium in the solid state in one single loading operation.

10. A process according to claim 4, characterized in that the cobalt hydrocarbonyl salt catalyst is added in a quantity comprised between about 1:5 and 1:500, calculated as mols of cobalt with respect to the mols of halide (II).

11. A process according to claim 4, characterized in that the cobalt hydrocarbonyl salt catalyst is prepared "in situ" from $Co_2(CO)_8$ in the anhydrous alcoholic solvent in the presence of alkaline hydroxides.

12. A process according to claim 1, characterized in that the starting halide of formula (II), as defined in claim 1, is selected from the groups consisting of: 1-bromo-1-phenylethane, 1-chloro-1-phenyletane; 1-bromo-1-(p.chlrorophenyl)-ethane; 1-chloro-1-(6'-methoxy-2'-naphthyl)-ethane, 1-chloro-1-(p.isobutylphenyl)-ethane.

13. The process of claim 1, in which Ar is selected from the group consisting of phenyl, naphthyl, diphenyl and thienyl groups and said groups carrying substituents inert under the reaction conditions.

14. The process of claim 13, in which the substituents inert under the reaction conditions are selected from the group consisting of alkyl, cycloalkyl and aryl groups, halogens, and alkoxyl and, phenoxyl groups.

15. The process of claim 4, in which Me in formula (III) is a metal selected from the group consisting of Na, K, Li, Co, Mn and Fe.

16. The process of claim 10, in which the cobalt hydrocarbonyl salt catalyst is added in an amount of from about 1:10 to 1:20, calculated as mols of cobalt with respect to the mols of halide (II).

* * * * *